United States Patent [19]

Chirikjian et al.

[11] Patent Number: 5,776,684
[45] Date of Patent: Jul. 7, 1998

[54] METHOD FOR STAINING BIOMOLECULES USING A GELLED MATRIX

[75] Inventors: Jack C. Chirikjian, Potomac; Gordon Bruce Collier, Gaithersburg, both of Md.

[73] Assignee: Edvotek, West Bethesda, Md.

[21] Appl. No.: 580,253

[22] Filed: Dec. 28, 1995

[51] Int. Cl.$^6$ .............................. C12Q 1/68; G01N 33/48
[52] U.S. Cl. .................. 435/6; 436/86; 436/94; 436/501
[58] Field of Search .................. 435/6; 422/61, 422/82.08, 99, 104; 436/501, 86, 94

[56] References Cited

U.S. PATENT DOCUMENTS

| | | | |
|---|---|---|---|
| 3,930,880 | 1/1976 | Hoefer | 134/111 |
| 4,613,566 | 9/1986 | Potter | 435/6 |
| 4,880,741 | 11/1989 | Davidow et al. | 435/172.3 |

*Primary Examiner*—Kenneth R. Horlick
*Attorney, Agent, or Firm*—Sana A. Pratt; Pratt & Associates

[57] ABSTRACT

A new method for staining biomolecules is described wherein a prepared gelled matrix containing the desired stain is applied onto the biomolecules such that the stain is transferred from the gelled matrix to the biomolecules. This method eliminates the potential hazard of exposing the technician or researcher to the staining solution itself and avoids environmental contamination resulting from the disposal of the staining solution in the water supply.

3 Claims, 1 Drawing Sheet

Cross-section

Cross-section

METHOD FOR STAINING BIOMOLECULES USING A GELLED MATRIX

INTRODUCTION

Electrophoresis techniques have become principal tools for characterizing biomolecules. The method is based on the fact that macromolecules such as DNA, RNA and proteins possess a charge and can therefore move in an electric field through sieving materials such as agarose or acrylamide. The application of electrophoretic techniques has required the development of staining methods to visualize the separated macromolecules such as ethidium bromide (EtBr) to visualize DNA. The disadvantage of this widely used stain is that it is a potent mutagen. The potential personal hazard of directly contacting such a solution and the environmental hazard of pouring an EtBr solution or other hazardous chemicals down the drain has resulted in a need for a better and safer method of preparing, using and disposing of such toxic solutions.

SUMMARY OF THE INVENTION

The present invention is directed to a process which satisfied this need. The present invention describes a process for staining biomolecules without having direct contact with the staining solution itself, as well as avoiding environmental contamination resulting from the disposal of the toxic staining solution and into water supplies.

The process of the present invention comprises applying a gelled matrix containing the stain onto a gel or support containing the biomolecule such that the stain diffuses from the matrix to the biomolecules on the gel or support. This process eliminates the environmental hazard due to disposal of toxic stains down the drain since the gelled matrix can be disposed of in the solid chemical waste container. In addition, the process reduces the amount of stain to be used and eliminates the personal hazards associated with staining biomolecules since the operator will no longer need to have direct contact with the staining solution itself.

More specifically, the present invention describes a process for staining DNA with EtBr without having direct contact with the EtBr solution itself, as well as avoiding environmental contamination. More specifically, the process of the present invention comprises applying a prepared gelled matrix shaped to fit the electrophoretic gel to a DNA separation gel to effect direct transfer of EtBr from the gelled matrix to the separation gel thereby intercalating the DNA making it fluoresce when exposed to ultraviolet (UV) light and then disposing of the gelled matrix in solid chemical waste.

Therefore, it is one object of the present invention to provide a general process for staining biomolecules comprising applying a gelled matrix containing the stain onto a gel or support containing the biomolecule such that the stain diffuses from the matrix to the biomolecules on the gel or support.

It is another object of the present invention to provide a process for staining DNA without having direct contact with EtBr and without contaminating the environment.

It is a further object of the present invention to provide a gelled matrix for staining biomolecules comprising a gelled matrix containing the desired stain. The gelled matrix may further be comprised of a mesh and a support.

It is yet another object of the present invention to provide a staining kit comprised of a gelled matrix containing the desired stain and ancillary reagents to effect staining of the biomolecules.

It is still another object of the present invention to provide a method for detecting specific biomolecules on a membrane comprising applying a gelled matrix containing a labeled probe which specifically recognizes the biomolecules to be detected, allowing the probe to diffuse from the gelled matrix to the membrane, and detecting the complex formed between the biomolecules and the labeled probe specific therefor.

DETAILED DESCRIPTION

The present invention relates to a new process for staining biomolecules. The process will be described in detail in connection with staining DNA with EtBr, but it is understood that DNA can be replaced by any biomolecule and similarly, EtBr can be replaced by the stain desired.

Therefore, more specifically, the present invention relates to a new process for staining biomolecules, for example DNA. The process is comprised of the steps of applying a gelled matrix containing the desired stain, for example EtBr, to an electrophoretic gel on which DNA fragments were fractionated, and allowing the EtBr to diffuse from the gel matrix to the electrophoretic gel thereby staining the DNA.

The gelled matrix can be composed of any molecule which would effect even transfer of the stain. For example, the gelled matrix can be composed of agarose and locust bean gum, or agarose and guar gum, or agarose and tara gum as a combination of dry powders in the ratio of about 9:1 to 5:5, most preferably about 5:3. Alternatively, a matrix can be used such as a matrix composed of gellan gum or pectin at a concentration of about 0.5 to 4% by weight aqueous solution, preferably at about 2% by weight aqueous solution. When using such a matrix, a divalent cation such as $Ca^{+2}$, can be added at a concentration of about 1 to 20 mM, preferably about 5 mM. The solution is heated until the gel goes into solution and then cast into a gel forming apparatus to generate the shape of the final gelled matrix which is shaped to cover the biomolecules to be stained such as an electrophoretic gel, for example. Heating the gel can be by microwaving or by any other conventional heat source. The stain, whether powder or solution, can be added prior to or after dissolving the gel particles by heat. Any gel casting apparatus can be used as long as the shape and size fits the area of the electrophoretic gel to be stained. The thickness of the resulting gelled matrix can be from about 1–5 mm.

Figure 1:
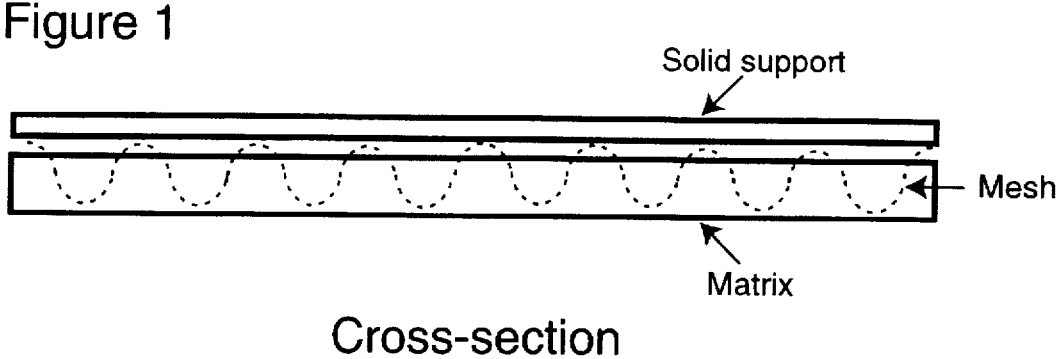
FIG. 1 shows a cross section of the gelled matrix with the mesh interwoven in the gelled matrix. The mesh is weaved through the center of the matrix with both ends of the mesh protruding out of the matrix at D and E, such that the mesh enters and extends into about the center of the matrix, then extends out one side, side A, of the matrix, reenters the matrix at B, leaving a portion of the mesh exposed on side A, extends into the matrix again, protruding out of matrix at C, and so on for the length of the matrix. A solid support is attached to the mesh through the portions of the mesh extruding from the gelled matrix at side A.
Figure 2:
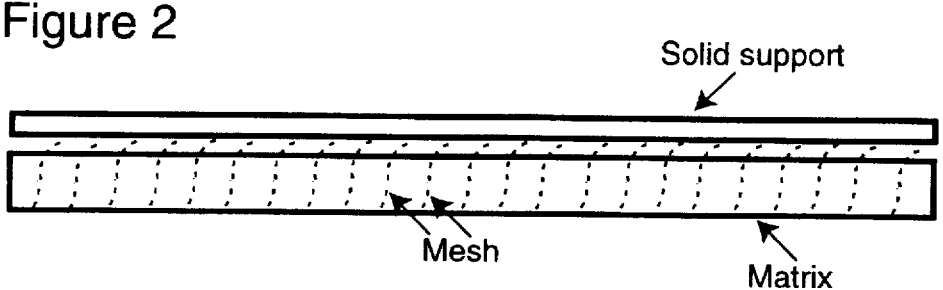
FIG. 2 shows a cross section of the gelled matrix with the mesh imbedded into and through the matrix in a vertical direction (or in the direction of the thickness of the matrix). Individual units of mesh are embedded in plurality across the length of the matrix. The mesh inserts through the top of the matrix (at A), through the matrix but does not exit through the bottom of the gel leaving a portion of the mesh exposed at the top to afford the ability to attach the mesh to a solid support. A plurality of mesh units are inserted across the length of the matrix dependent on its length as shown.

For increased strength of the matrix, a mesh can be inserted in the gelled matrix. The mesh can be inserted in the center of the gelled matrix prior to the hardening of the gelled matrix. Any nylon, cloth, or plastic mesh can be used which is flexible, strong enough to not rip upon moving so as to provide a mechanism for transporting the matrix, and chemically and temperature stable for this application. The mesh can be nylon, cotton, rayon, polyester, polyethylene, or polypropylene, for example. The mesh can be applied in several ways, two of which are shown in FIGS. 1 and 2. In FIG. 1, the mesh is weaved through the center of the matrix with both ends of the mesh extruding out of the matrix (point D and E), such that the mesh enters and extends into about the center of the matrix, then extends out of one side (side A) of the matrix, then reenters the matrix at another point (point B) extending into the center of the matrix again and extending out side A at point C and so on for the length of the matrix. In FIG. 2, a mesh is embedded into and through the matrix in a vertical direction (the thickness of the matrix). The mesh inserts through the top of the matrix, through the matrix, but does not exit through the bottom of the gel. The mesh inserts from 50 to 90% of the thickness of the matrix. Individual units of mesh are added in plurality across the length of the matrix, the number of units dependent on the length of the matrix, usually greater than four.

The portion of the mesh exposed at the top in FIGS. 1 and 2 is just long enough to afford the ability to attach the mesh to a solid support. This attachment can be effected by gluing, sewing, riveting, binding, or welding by sonication the exposed mesh to the solid support, by methods known to those skilled in the art. The solid support affords support in the longitudinal direction, preventing the matrix from bending to differing degrees, dependent on the material used as the solid support. The support can be any wood, preferably light and strong such as Balsam of about $1/16-1/8$ of an inch in thickness, any plastic, such as polypropylene or polyethylene of about 5–20 mm in thickness, any glass, such as borosilicate of about 50 mm, or any paper or cellulose-based compound such as wood or cotton at about 100 lb./square foot, for example, Whatman 3M paper. The support is linked to the mesh by gluing using Krazy glue (Borden, Inc., Columbus, Ohio) for example, by sewing using a nylon, plastic, cloth, or metal thread.

The matrix described above is applied onto the electrophoretic gel to be stained such that the matrix is in contact with the biomolecule, for example DNA, and the stain, for example EtBr, can diffuse from the matrix to the gel and intercalate into the DNA. Usually, this requires about 5 minutes or longer of direct contact. The gel containing the biomolecules can be made of any sieving material such as agarose or acrylamide. Any stain for any biomolecule can be incorporated into the gelled matrix such as YoYo (Molecular Probes, Inc., Boulder, Colo.), Toto (Molecular Probes, Inc., Boulder Colo.), Methylene blue, Stains-All (Sigma), Coomassie Brilliant blue, to name a few.

After the electrophoretic gel is stained, the gelled matrix is peeled off. If the gelled matrix includes the mesh/support, the mesh/support can be used to peel the matrix off of the electrophoretic gel or biomolecules, and disposed of in the solid chemical waste. In this process, the researcher has no direct contact with a toxic staining solution such as EtBr, the volume of EtBr is minimized, and disposal in a solid disposal system saves the environment from any hazards such a staining solution may produce.

In another embodiment, the present invention relates to a process for delivering biomolecules from a gelled matrix to a nitrocellulose membrane onto which DNA or RNA, or protein has been transferred for the purpose of detecting specific DNA fragments, RNA or protein such as in the Southern, northern, or western hybridization assay well known to a person with ordinary skill in the art. The gelled matrix can be prepared as above with the addition of dextran sulfate. For example, a gel matrix of agarose, locust bean gum and dextran sulfate would be prepared in a combination of dry powders in the ratio of about 5 to 3 to a range of about 0.5 to 3 of dextran sulfate, preferably about 1. Instead, or in addition to adding a stain, a labeled synthetic oligonucleotide, or probe, complementary to the DNA fragment or RNA species to be detected is added prior to or after dissolving the gel. The oligonucleotide can be labeled with a radioactive label or a nonradioactive label such as biotin. The labeled probe can be added at a concentration of from about 1–1000 pmol/ml, preferably about 100 pmol/ml. After transfer of the electrophoresed DNA onto a nitrocellulose or nylon membrane as is usually done in a Southern or northern transfer, the gelled matrix containing the labeled probe is applied to the nylon membrane such that the gelled matrix is in direct contact with the DNA fragments to be detected and even transfer of the probe from the gelled matrix to the DNA separation gel is effected. The matrix and the gel are left in contact for about one hour up to eighteen hours or overnight, and then separated. The presence of a complex formed between the probe and the complementary DNA or RNA fragment on the gel is detected by methods known in the art for the type of label used. This method can also be applied to western transfers for the detection of proteins separated on a gel and transferred to a membrane. The label to be used can be alkaline phosphatase, horseradish peroxidase or a chemiluminescent reagent.

In yet another embodiment, the present invention relates to a kit for delivering stains to biomolecules, comprising a matrix gel having a desired stain and a nylon mesh in center of the matrix, and ancillary reagents to effect staining of the biomolecules. The kit can be an educational or research kit whereby other reagents for the preparation of the separation gels are included as well as other reagents for the detection of the stained biomolecules, for example enzymes. When the kit contains a gel matrix with EtBr for staining DNA or RNA, the gel must be stored such that it is not exposed to light since EtBr is light sensitive.

Described below are examples of the present invention which are provided only for illustrative purposes, and not to limit the scope of the present invention. In light of the present disclosure, numerous embodiments within the scope of the claims will be apparent to those of ordinary skill in the art.

EXAMPLE 1

Delivery of EtBr from an agarose and locust bean gum matrix

A gel matrix was composed of agarose and locust bean gum and was prepared as a combination of dry powders of agarose to locust bean gum in the ratio of 5 to 3 by mass, respectively. This mixture was mixed thoroughly by rolling or shaking. Two grams of this powder was added to deionized water, then microwaved until the powder went completely into solution. The criteria for dissolving was ascertained by visual inspection of the solution. The water lost from heating was replaced, then ethidium bromide was added to a final concentration of 0.5 µg/ml. A nylon mesh with approximately 1 mm sized meshed holes was placed horizontally along the length of the gel casting tray. Portions of the nylon mesh were pulled out of the top of the matrix at points along the matrix. This effected an undulating pattern (see FIG. 1) of the nylon mesh horizontally along the matrix, with short portions exiting the gel at the top and other portions remaining in the center of the matrix. The matrix was allowed to cool and harden before proceeding to the next stage in the process.

The hardened matrix was removed from the casting tray. Krazy Glue was applied to the portions of the nylon mesh available at the top of the matrix where it protrudes through. A piece of polypropylene plastic support the size of the cast gel was then placed on top of the matrix. The portions of the nylon mesh with Krazy Glue fused to the polypropylene plastic, effected a linked matrix to a polypropylene plastic support, through the nylon mesh.

Once the glue had set, the matrix, as prepared above, was then applied to an agarose or similar DNA separation gel (e.g. TreviGel™ 500, Trevigen, Inc.) to effect even transfer of the ethidium bromide from the above cast matrix to the DNA separation gel. The two matrices are left in contact for five minutes, then separated. The DNA separation gel was then subjected to Ultraviolet illumination, allowing the detection of DNA where the ethidium bromide intercalates with the DNA.

By using the gelled matrix, the DNA was stained without exposing the researcher or the environment to the toxic ethidium bromide solution.

EXAMPLE 2

Delivery of EtBr from an agarose and guar gum matrix

A gel matrix is composed of agarose and guar gum and was prepared as a combination of dry powders of agarose to locust bean gum in the ratio of 5 to 3, respectively. A 2% by weight aqueous solution was prepared with a final concentration of ethidium bromide which can range from 0.05 to 5 $\mu g \cdot ml^{-1}$, heated by microwaving until the gel went into solution, then cast into a gel forming apparatus to generate the shape of the final gelled matrix, which is shaped to fit an electrophoretic gel. In the center of the matrix is a nylon mesh woven through the matrix on side providing strength and a means for holding and moving the matrix.

The matrix prepared as above is then applied to an agarose or similar DNA separation gel to effect even transfer of the ethidium bromide from the above cast matrix to the DNA separation gel. The two matrices are left in contact for five minutes, then separated. The DNA separation gel is then subjected to UV illumination, allowing the detection of DNA where the ethidium bromide intercalates with the DNA.

EXAMPLE 3

Delivery of EtBr from an agarose and tara gum matrix

A gel matrix is composed of agarose and tara gum was prepared as a combination of dry powders of agarose to locust bean gum in the ratio of 5 to 3, respectively. A 2% by weight aqueous solution was prepared with a final concentration of ethidium bromide which can range from 0.05 to 5 $\mu g \cdot ml^{-1}$, heated by microwaving until the gel went into solution, then cast into a gel forming apparatus to generate the shape of the final gelled matrix, which is shaped to fit an electrophoretic gel. In the center of the matrix is a nylon mesh woven through the matrix on side providing strength and a means for holding and moving the matrix.

The matrix prepared as above is then applied to an agarose or similar DNA separation gel to effect even transfer of the ethidium bromide from the above cast matrix to the DNA separation gel. The two matrices are left in contact for five minutes, then separated. The DNA separation gel is then subjected to UV illumination, allowing the detection of DNA where the ethidium bromide intercalates with the DNA.

EXAMPLE 4

Delivery of EtBr from a gellan gum matrix

A gel matrix composed of gellan gum was used to generate a specialized matrix format. A 2% by weight aqueous solution was prepared with a final concentration of ethidium bromide which can range from 0.05 to 5 $\mu g \cdot ml^{-1}$, calcium chloride was added to effect gel hardening and it was cast into a gel forming apparatus to generate the shape of the final gelled matrix, which is shaped to fit an electrophoretic gel. In the center of the matrix is a nylon mesh that aids in the strength of the matrix.

The matrix prepared as above is then applied to an agarose or similar DNA separation gel to effect even transfer of the ethidium bromide from the above cast matrix to the DNA separation gel. The two matrices are left in contact for five minutes, then separated. The DNA separation gel is then subjected to UV illumination, allowing the detection of DNA where the ethidium bromide intercalates with the DNA.

EXAMPLE 5

Delivery of EtBr from a pectin matrix

A gel matrix composed of pectin was used to generate a specialized matrix format. A 2% by weight aqueous solution was prepared with a final concentration of ethidium bromide which can range from 0.05 to 5 $\mu g \cdot ml^{-1}$, calcium chloride was added to effect gel hardening and it was cast into a gel forming apparatus to generate the shape of the final gelled matrix, which is shaped to fit an electrophoretic gel. In the center of the matrix is a nylon mesh that aids in the strength of the matrix.

The matrix prepared as above is then applied to an agarose or similar DNA separation gel to effect even transfer of the ethidium bromide from the above cast matrix to the DNA separation gel. The two matrices are left in contact for five minutes, then separated. The DNA separation gel is then subjected to UV illumination, allowing the detection of DNA where the ethidium bromide intercalates with the DNA.

EXAMPLE 6

Delivery of methylene blue or other ionic dyes from an agarose and locust bean gum matrix A gel matrix composed of agarose and locust bean gum was prepared as a combination of dry powders of agarose to locust bean gum in the ratio of 5 to 3, respectively. A 2% by weight aqueous solution was prepared with a final concentration of methylene blue which can range from 0.05 to 5 $\mu g \cdot ml^{-1}$, heated by microwaving until the gel went into solution, then cast into a gel forming apparatus to generate the shape of the final gel matrix, which is shaped to fit an electrophoretic gel. In the center of the matrix is a nylon mesh that aids in the strength of the matrix.

The matrix prepared as above is then applied to an agarose or similar DNA separation gel to effect even transfer of the methylene blue from the above cast matrix to the DNA separation gel. The two matrices are left in contact for five minutes, then separated.

EXAMPLE 7

Delivery of methylene blue from an agarose and guar gum matrix

A gel matrix is composed of agarose and guar gum was prepared as a combination of dry powders of agarose to locust bean gum in the ratio of 5 to 3, respectively. A 2% by weight aqueous solution was prepared with a final concentration of methylene blue which can range from 0.05 to 5 µm·ml$^{-1}$, heated by microwaving until the gel went into solution, then cast into a gel forming apparatus to generate the shape of the final gelled matrix, which is shaped to fit an electrophoretic gel. In the center of the matrix is a mesh that aids in the strength of the matrix.

The matrix prepared as above is then applied to an agarose or similar DNA separation gel to effect even transfer of the methylene blue from the above cast matrix to the DNA separation gel. The two matrices are left in contact for five minutes, then separated.

EXAMPLE 8

Delivery of methylene blue from an agarose and tara gum gelled matrix

A gel matrix composed of agarose and tara gum was prepared as a combination of dry powders of agarose to locust bean gum in the ratio of 5 to 3, respectively. A 2% by weight aqueous solution was prepared with a final concentration of methylene blue which can range from 0.05 to 5 µg·ml$^{-1}$, heated by microwaving until the gel went into solution, then cast into a gel forming apparatus to generate the shape of the final gelled matrix, which is shaped to fit an electrophoretic gel. In the center of the matrix is a mesh that aids in the strength of the matrix.

The matrix prepared as above is then applied to an agarose or similar DNA separation gel to effect even transfer of the methylene blue from the above cast matrix to the DNA separation gel. The two matrices are left in contact for five minutes, then separated.

EXAMPLE 9

Delivery of methylene blue from a gellan gum specialized matrix

A gel matrix composed of gellan gum was used to generate a specialized matrix format. A 2% by weight aqueous solution was prepared with a final concentration of methylene blue which can range from 0.05 to 5 µg·ml$^{-1}$, calcium chloride was added to effect gel hardening and it was cast into a gel forming apparatus to generate the shape of the final gelled matrix, which is shaped to fit an electrophoretic gel. In the center of the matrix is a mesh that aids in the strength of the matrix.

The matrix prepared as above is then applied to an agarose or similar DNA separation gel to effect even transfer of the methylene blue from the above cast matrix to the DNA separation gel. The two matrices are left in contact for five minutes, then separated.

EXAMPLE 10

Delivery of methylene blue from a pectin specialized matrix

A gel matrix is composed of pectin was used to generate a specialized matrix format. A 2% by weight aqueous solution was prepared with a final concentration of methylene blue which can range from 0.05 to 5 µg·ml$^{-1}$, calcium chloride was added to effect gel hardening and it was cast into a gel forming apparatus to generate the shape of the final gelled matrix, which is shaped to fit an electrophoretic gel. In the center of the matrix is a nylon mesh that aids in the strength of the matrix.

The matrix prepared as above is then applied to an agarose or similar DNA separation gel to effect even transfer of the methylene blue from the above cast matrix to the DNA separation gel. The two matrices are left in contact for five minutes, then separated.

EXAMPLE 11

Delivery of biotinylated synthetic oligonucleotide

A gel matrix composed of agarose, locust bean gum and dextran sulfate was prepared as a combination of dry powders of agarose to locust bean gum to dextran sulfate in the ratio of 5 to 3 to 1, respectively. A 2% by weight aqueous solution was prepared with a final concentration of 100 µg·ml$^{-1}$, of biotinylated synthetic oligonucleotide which hybridizes to the human B-actin gene, heated by microwaving until the gel went into solution, then cast into a gel forming apparatus to generate the shape of the final gelled matrix, which is shaped to fit an electrophoretic gel. In the center of the matrix is a nylon mesh that aids in the strength of the matrix.

The matrix prepared as above is then applied to a nylon membrane wherein the DNA from an agarose or similar DNA separation gel was transferred by the Southern transfer technique, well known to those skilled in the art. The above prepared matrix with biotinylated probe was put in contact with the DNA containing membrane to effect even transfer of the biotinylated probe from the above cast matrix to the DNA separation gel. The two matrices are left in contact for one hour, then separated. The DNA containing membrane is then treated with a streptavidin-Horseradish peroxidase conjugate. The membrane is washed with an excess of 1×PBS to remove unbound streptavidin-Horseradish peroxidase conjugate. A tetramethylbenzidine containing solution is then reacted with the membrane, allowing the development of a blue substrate by the enzymatic reaction of the Horseradish peroxidase, indicating the presence of the specific DNA fragment.

EXAMPLE 12

Delivery of a radioactively labeled synthetic oligonucleotide

A gel matrix composed of agarose, locust bean gum and dextran sulfate was prepared as a combination of dry powders of agarose to locust bean gum to dextran sulfate in the ratio of 5 to 3 to 1, respectively. A 2% by weight aqueous solution was prepared with a final concentration of 100 µg·ml$^{-1}$, of radioactively labeled synthetic oligonucleotide which hybridizes to the human β-actin gene, heated by microwaving until the gel went into solution, then cast into a gel forming apparatus to generate the shape of the final gelled matrix, which is shaped to fit an electrophoretic gel. In the center of the matrix is a nylon mesh that aids in the strength of the matrix.

The matrix prepared as above is then applied to a nylon membrane wherein the DNA from an agarose or similar DNA separation gel was transferred by the Southern transfer technique, well known to those skilled in the art. The above prepared matrix with radioactively labeled probe was put in contact with the DNA containing membrane to effect even transfer of the radiolabeled probe from the above cast matrix to the DNA separation gel. The two matrices are left in contact for one hour, then separated. The DNA containing "membrane is then prepared for autoradiography in order to visualize and quantitate on film radioactive molecules hybridized to the membrane."

Although the present invention has been described with considerable detail with reference to certain preferred versions thereof, other versions are possible and within the capability of those in the art. Therefore, the spirit and scope of the appended claims should not be limited to the description of the preferred versions contained herein.

What is claimed is:

1. A method for staining biomolecules with a desired stain, said method comprising the steps of:
   (i) applying a gelled matrix containing the desired stain distributed evenly therein to a gel or support containing said biomolecules;
   (ii) allowing said stain to diffuse from the gelled matrix to said biomolecules; and
   (iii) removing said gelled matrix from said gel or support.

2. A method for staining DNA with EtBr, said method comprising the steps of:
   (i) applying a gelled matrix containing EtBr distributed evenly therein to a gel or support containing said DNA;
   (ii) allowing EtBr to diffuse from the gelled matrix to said DNA; and
   (iii) removing said gelled matrix from said gel or support.

3. A method for detecting specific DNA fragments present on a membrane, said method comprising the steps of:
   (i) applying to said membrane a gelled matrix containing a labeled probe distributed evenly therein capable of hybridizing specifically with the DNA fragments to be detected;
   (ii) allowing the probe to diffuse from the gelled matrix to the membrane under hybridizing conditions; and
   (iii) detecting a complex formed between the DNA fragments and the labeled probe specific therefor.

* * * * *